(12) United States Patent
Shibata et al.

(10) Patent No.: US 11,246,825 B2
(45) Date of Patent: Feb. 15, 2022

(54) SOLID WAX COMPOSITION AND SOLID OILY COSMETIC

(71) Applicant: The Nisshin OilliO Group, Ltd., Tokyo (JP)

(72) Inventors: Masashi Shibata, Tokyo (JP); Daisuke Shimizu, Yokohama (JP); Hisanori Kachi, Yokohama (JP)

(73) Assignee: The Nisshin OilliO Group, Ltd., Tokyo (JP)

( * ) Notice: Subject to any disclaimer, the term of this patent is extended or adjusted under 35 U.S.C. 154(b) by 0 days.

(21) Appl. No.: 16/448,991

(22) Filed: Jun. 21, 2019

(65) Prior Publication Data

US 2019/0307672 A1 Oct. 10, 2019

Related U.S. Application Data

(63) Continuation of application No. PCT/JP2017/046008, filed on Dec. 21, 2017.

(30) Foreign Application Priority Data

Dec. 27, 2016 (JP) .............................. JP2016-253000

(51) Int. Cl.
| | |
|---|---|
| *A61K 8/92* | (2006.01) |
| *A61K 8/37* | (2006.01) |
| *A61Q 19/00* | (2006.01) |
| *A61Q 1/06* | (2006.01) |
| *C08L 91/06* | (2006.01) |
| *A61Q 1/00* | (2006.01) |

(52) U.S. Cl.
CPC ................ *A61K 8/922* (2013.01); *A61K 8/37* (2013.01); *A61K 8/92* (2013.01); *A61Q 1/00* (2013.01); *A61Q 1/06* (2013.01); *A61Q 19/00* (2013.01); *A61Q 19/001* (2013.01); *C08L 91/06* (2013.01)

(58) Field of Classification Search
None
See application file for complete search history.

(56) References Cited

U.S. PATENT DOCUMENTS

| 4,393,044 | A | 7/1983 | Takata et al. | |
|---|---|---|---|---|
| 2009/0196842 | A1* | 8/2009 | Zech | A61K 8/92 424/70.7 |
| 2011/0243863 | A1 | 10/2011 | Kawa et al. | |

FOREIGN PATENT DOCUMENTS

| DE | 102008052520 A1 | 4/2010 |
|---|---|---|
| JP | S56-167611 A | 12/1981 |
| JP | S57-004908 A | 1/1982 |
| JP | S61-210054 A | 9/1986 |
| JP | H02-264712 A | 10/1990 |
| JP | 2003-063919 A | 3/2003 |
| JP | 2004-224707 A | 8/2004 |
| JP | 2005-314257 A | 11/2005 |
| JP | 2006-342141 A | 12/2006 |
| JP | 2006-342142 A | 12/2006 |
| JP | 2007-112727 A | 5/2007 |
| JP | 2007112727 A * | 5/2007 |
| JP | 2009-234991 A | 10/2009 |
| JP | 2009-234992 A | 10/2009 |

OTHER PUBLICATIONS

English language translation of JP 2007-112727 A. (Year: 2007).*
Handbook of Oil and Fat Chemistry, revised third edition, The Japan Oil Chemists' Association, published by Maruzen Co., Ltd., Feb. 28, 1990, p. 135, Table 2.52 (Year: 1990).*
Cummings et al., "A natural alternative", reprinted from SPC Asia, May 1, 1999, XP055695686, Retrieved from the Internet: URL: https://www.floratech.com/PDFs/Articles_MKT/ART15.pdf [retrieved on May 14, 2020].
Bergfeld et al., Final Report of the Cosmetic Ingredient Review Expert Panel, Safety Assessment of Simmondsia Chinensis (Jojoba) Seed Oil, Simmondsia Chinensis (Johoba) Seed Wax, Hydrogentated Jojoba Oil, Hydrolyzed Jojoba Esters, Isomerized Jojoba Oil, Jojoba Esters, Simmondsia Chinensis (Jojoba) Butter, Jojoba Alcohol, and Synthetic Jojoba Oil, Sep. 23, 2008, XP055695687, Retrieved from the Internet: URL: https://www.cir-safety.org/sites/default/files/115_buff3f_suppl.pdf [retrieved on May 14, 2020].
Extended European Search Report issued in corresponding European Patent Application No. 17887867.4, dated May 27, 2020.
Shibata et al., "Technology of compatibility between stability and feel in lip cosmetics," Fragrance Journal 40 (1): 59-64 (2012) (with English abstract).
International Search Report issued in corresponding International Patent Application No. PCT/JP2017/046008 dated Mar. 13, 2018.

* cited by examiner

*Primary Examiner* — Dominic Lazaro
(74) *Attorney, Agent, or Firm* — Morgan, Lewis & Bockius LLP

(57) ABSTRACT

The present invention provides a composition that has an excellent hardness adjustment action, can be used as a solidifying agent for various cosmetics, and when added to cosmetics, can impart those cosmetics with excellent shape retention properties, an oil oozing suppression effect during use, a favorable texture and good storage stability, and also provides an oily solid cosmetic to which the composition has been added. Specifically, the invention provides a solid wax composition containing a component (A): candelilla wax, and a component (B): a monoester having a total of 40 to 48 carbon atoms, wherein the mass ratio between the component (A) and the component (B) in the solid wax composition satisfies component (A):component (B)=45:55 to 95:5, and the monoester is a monoester of a monovalent fatty acid and a monohydric alcohol.

31 Claims, No Drawings

SOLID WAX COMPOSITION AND SOLID OILY COSMETIC

TECHNICAL FIELD

The present invention relates to a solid wax composition that has an excellent hardness adjustment action and can be used as a solidifying agent for various cosmetics, and also relates to a solid oily cosmetic to which the solid wax composition has been added.

Priority is claimed on Japanese Patent Application No. 2016-253000, filed Dec. 27, 2016, the content of which is incorporated herein by reference.

BACKGROUND ART

Oily solid cosmetics typified by lipsticks can be adjusted to the desired hardness by increasing or decreasing the amount of wax added. Among the various options, polyethylene wax, paraffin wax, candelilla wax and carnauba wax are commonly used to increase the hardness. Although these waxes enable the desired hardness to be achieved by adding only a small amount of wax, because they do not break down smoothly during use, and the liquid oil can cause oil ooze, they tend to suffer from an inferior texture and are prone to makeup deterioration.

As a result, in order to suppress oil oozing during use, the addition to the liquid oil of a combination of a linear hydrocarbon wax having a powerful oil solidification function and a hydrocarbon wax having side chains has been disclosed (Non-Patent Document 1). However, hydrocarbon waxes having side chains have low crystallinity, and therefore oily solid cosmetics containing an added hydrocarbon wax having side chains have sometimes suffered from poor storage stability and an inferior texture.

CITATION LIST

Non-Patent Documents

Non-Patent Document 1: Masashi Shibata, Fragrance Journal, Jan. 15, 2012, Vol. 40, No. 1, pp. 59 to 64.

SUMMARY OF THE INVENTION

Problems to be Solved by the Invention

Objects of the present invention are to provide a solid wax composition that has an excellent hardness adjustment action, can be used as a solidifying agent for various cosmetics, and when added to cosmetics, can impart those cosmetics with excellent shape retention properties, an oil oozing suppression effect during use, a favorable texture and good storage stability, and also to provide an oily solid cosmetic to which the composition has been added.

Means for Solving the Problems

The inventors of the present invention discovered that by using a solid wax composition in which candelilla wax and a monoester having a specific structure have been combined in a specific ratio, when the solid wax composition is mixed with a liquid oil, excellent shape retention properties, an oil oozing suppression effect during use, a favorable texture and good storage stability could be imparted, and they were therefore able to complete the present invention.

In other words, a solid wax composition and a solid oily cosmetic according to the present invention are as described below in [1] to [5].

[1] A solid wax composition containing a component (A): candelilla wax, and a component (B): a monoester having a total of 40 to 48 carbon atoms, wherein the mass ratio between the component (A) and the component (B) in the solid wax composition satisfies component (A):component (B)=45:55 to 95:5, and the monoester is a monoester of a monovalent fatty acid and a monohydric alcohol.

[2] The solid wax composition of [1] above, wherein the monoester of the component (B) is composed of one type, or two or more types, of monoester selected from the group consisting of monoesters of a linear saturated fatty acid of 18 to 22 carbon atoms and a linear saturated aliphatic alcohol of 18 to 22 carbon atoms, and hydrogenated jojoba oil.

[3] The solid wax composition of [2] above, wherein the monoester of a linear saturated fatty acid of 18 to 22 carbon atoms and a linear saturated aliphatic alcohol of 18 to 22 carbon atoms is behenyl behenate.

[4] The solid wax composition of any one of [1] to [3] above, wherein the proportion representing the sum of the amounts of the component (A) and the component (B) relative to the total mass of the composition is at least 90% by mass.

[5] A solid oily cosmetic containing a component (A): candelilla wax, and a component (B): a monoester having a total of 40 to 48 carbon atoms, wherein the mass ratio between the component (A) and the component (B) in the solid oily cosmetic satisfies component (A):component (B)=45:55 to 95:5, and the monoester is a monoester of a monovalent fatty acid and a monohydric alcohol.

Effects of the Invention

The solid wax composition according to the present invention has an excellent hardness adjustment action, can be used as a solidifying agent for various cosmetics, and can impart cosmetics with excellent shape retention properties, an oil oozing suppression effect, favorable texture and good storage stability. Accordingly, the solid wax composition is ideal as a raw material for solid oily cosmetics, and particularly as a raw material for stick-type lipsticks and the like.

Further, in the solid oily cosmetic according to the present invention, by including a liquid oil, together with candelilla wax and a monoester having a specific structure in a specific ratio, a cosmetic is obtained that has excellent shape retention properties and storage stability, suppressed oil oozing, and a favorable texture.

EMBODIMENTS FOR CARRYING OUT THE INVENTION

Embodiments of the present invention are described below in detail.

In the present invention and the present description, a "monoester" for which no particular description is provided means an ester compound of a monovalent fatty acid and a monohydric alcohol.

<Solid Wax Composition>

A solid wax composition according to the present invention contains candelilla wax as a component (A) and a monoester having a total of 40 to 48 carbon atoms as a component (B). In the present invention and the present description, a "solid wax composition" means a composition that contains a wax as a main component and is solid at normal temperature (20° C.).

Candelilla wax is a wax collected from the candelilla plant of the Euphorbia family (Euphorbia cerifera Alcocer) that grows on the plateaus of Central and South America. There are no particular limitations on the candelilla wax of the component (A), provided it is a wax that has been collected from the candelilla plant, and conventionally known products may be used. For example, a wax obtained by further purifying a crudely purified product prepared by removing contaminants from a wax extracted by a melt extraction method from candelilla plant that has been dried in the sun may be used as the candelilla wax of the component (A). Examples of the purification treatment performed on the crudely purified product include resin content removal, decolorization and deodorization, and these treatments may also be combined. The composition of candelilla wax is generally 24 to 30% by mass of wax esters of 42 to 56 carbon atoms, 10 to 20% by mass of free fatty acids of 20 to 35 carbon atoms, 10 to 15% by mass of free alcohols of 26 to 34 carbon atoms, and 40 to 50% by mass of hydrocarbons of 28 to 33 carbon atoms. For example, the candelilla wax disclosed in the Japanese Standards of Quasi-drug Ingredients 2006 is ideal as the component (A) used in the present invention.

Much of the candelilla wax that is typically available contains about 1% by mass of the monoester having a total of 40 to 48 carbon atoms of the component (B), but because that amount is very small, it has almost no influence on the effects of the present invention, and can be ignored. Accordingly, in the present invention and the present description, the small amount of monoester having a total of 40 to 48 carbon atoms derived from raw material in the candelilla wax of the component (A) is deemed to not be included in the monoester having a total of 40 to 48 carbon atoms of the component (B). Further, a candelilla wax containing a small amount of monoester having a total of 40 to 48 carbon atoms derived from the raw material may be used as the candelilla wax of the component (A).

There are no particular limitations on the monovalent fatty acid and the monohydric alcohol that function as the raw materials for the monoester having a total of 40 to 48 carbon atoms of the component (B), provided these raw materials can be used to obtain the monoester having a total of 40 to 48 carbon atoms via an esterification.

The monoester having a total of 40 to 48 carbon atoms of the component (B) is preferably a monoester obtained by the esterification of caprylic acid (octanoic acid), pelargonic acid (nonanoic acid), capric acid (decanoic acid), lauric acid (dodecanoic acid), myristic acid (tetradecanoic acid), pentadecylic acid (pentadecanoic acid), palmitic acid (hexadecanoic acid), margaric acid (heptadecanoic acid), stearic acid (octadecanoic acid), arachidic acid (eicosanoic acid), behenic acid (docosanoic acid), lignoceric acid (tetracosanoic acid), hexacosanoic acid, octacosanoic acid or triacontanoic acid, and decanol, undecanol, dodecanol, tridecanol, tetradecanol, pentadecanol, hexadecanol, heptadecanol, stearyl alcohol (octadecanol), nonadecyl alcohol (nonadecanol), arachidyl alcohol (eicosanyl alcohol), henicosyl alcohol, heneicosyl alcohol, behenyl alcohol (docosanyl alcohol), tricosanyl alcohol, lignoceryl alcohol (tetracosanyl alcohol), pentacosanyl alcohol, hexacosanyl alcohol, heptacosanyl alcohol, octacosanyl alcohol, nonacosanyl alcohol, triacontanyl alcohol, hentriacontanyl alcohol or dotriacontanyl alcohol.

In terms of obtaining a superior shape retention improvement effect and oil oozing suppression effect, the monoester having a total of 40 to 48 carbon atoms of the component (B) used in the present invention is preferably a monoester of a monovalent linear saturated fatty acid and a monohydric linear saturated aliphatic alcohol, and is more preferably a monoester of a monovalent linear saturated fatty acid of 18 to 22 carbon atoms and a monohydric linear saturated aliphatic alcohol of 18 to 22 carbon atoms. Specific examples of monoesters of a monovalent linear saturated fatty acid of 18 to 22 carbon atoms and a monohydric linear saturated aliphatic alcohol of 18 to 22 carbon atoms include behenyl stearate, arachidyl eicosanoate, henicosyl eicosanoate, behenyl eicosanoate, stearyl behenate, nonadecanyl behenate, arachidyl behenate, henicosyl behenate, and behenyl behenate.

The monoester of the component (B) included in the solid wax composition according to the present invention may be a chemically synthesized product, or may be a monoester having a total of 40 to 48 carbon atoms contained in an oil fraction extracted from a natural product such as a plant or microorganism, or in a modified product of such an oil fraction.

The monoester having a total of 40 to 48 carbon atoms of the component (B) can be synthesized by esterifying a monovalent fatty acid and a monohydric alcohol using conventionally known methods. For example, the monovalent fatty acid and monohydric alcohol may be placed in a reaction container in a molar ratio of 1:1, and then reacted by heating at 160 to 250° C. under an inert gas atmosphere while removing the water that is produced. At this time, a catalyst may or may not be used. Following the reaction, unreacted fatty acid or alcohol may be removed from the obtained reaction product if necessary. In those cases where a catalyst is used, the catalyst is also removed. The reaction product may then be subjected to purification such as decolorization or deodorization as necessary to obtain the monoester.

The monovalent fatty acid and the monohydric alcohol used in forming the monoester having a total of 40 to 48 carbon atoms of the component (B) that is included in the solid wax composition according to the present invention may be chemically synthesized compounds, or may be purified compounds obtained from an oil fraction extracted from a natural product such as a plant or microorganism. From the viewpoint of sustainability, the monovalent fatty acid and the monohydric alcohol that form the monoester having a total of 40 to 48 carbon atoms of the component (B) used in the present invention are preferably plant-derived components.

From an industrial viewpoint, the raw material containing the monoester of the component (B) used during production of the solid wax composition according to the present invention need not necessarily be a material of high purity, and may be a mixture with other components. Examples of materials (impurities) that may lower the amount within the raw material of the monoester having a total of 40 to 48 carbon atoms of the component (B) include monoesters and wax components other than the monoester having a total of 40 to 48 carbon atoms, and impurities or contaminants derived from the synthesis or purification of the monoester having a total of 40 to 48 carbon atoms of the component (B). For example, the reaction product obtained by reacting the monovalent fatty acid and the monohydric alcohol may be used, as is, as a raw material for the solid wax composition according to the present invention, or a purified product obtained by removing components other than the monoester having a total of 40 to 48 carbon atoms from the reaction product may be used. Furthermore, the solid wax composition according to the present invention may be produced by mixing the candelilla wax of the component (A) with an oil fraction extracted from a natural product such as a plant or microorganism, or a modified product of such an oil fraction, that contains the monoester of the component (B). Examples of oil fractions derived from natural products that contain a high concentration of the monoester having a total of 40 to 48 carbon atoms include hydrogenated jojoba oil and the like. The hydrogenated jojoba oil disclosed in the Japanese Standards of Quasi-drug Ingredients 2006 is preferably used as the hydrogenated jojoba oil used as the component (B).

The raw material containing the monoester of the component (B) used during production of the solid wax composition according to the present invention preferably contains a satisfactorily high content of the monoester of the component (B). This is because by using a raw material having a high content of the monoester of the component (B), the amounts of the component (A) and the component (B) in the solid wax composition can be satisfactorily increased, enabling the hardness adjustment action and the oil oozing suppression effect provided by the solid wax composition to be further enhanced. The raw material containing the monoester of the component (B) has a ratio of the amount (mass) of the monoester of the component (B) relative to the total mass of the raw material that is preferably at least 90% by mass but not more than 100% by mass, more preferably at least 94% by mass but not more than 100% by mass, and most preferably at least 96% by mass but not more than 100% by mass.

The amount of the monoester having a total of 40 to 48 carbon atoms of the component (B) within the solid wax composition, within the solid oily cosmetic described below, or within the raw material containing the monoester of the component (B) that is used in producing the solid wax composition or solid oily cosmetic, can be analyzed by conventionally known methods such as analytical methods using gas chromatography. For example, in an analytical method using gas chromatography, if the raw material containing the monoester of the component (B) is used as a measurement sample, and this measurement sample is subjected to gas chromatography analysis under the analysis conditions described below, then the ratio obtained by dividing the total peak area of those peaks appearing within the retention time range between the peaks corresponding with the main peaks of standard substances having a total of 40 and 48 carbon atoms respectively by the total area of all the peaks is the same as the ratio of the amount of the monoester having a total of 40 to 48 carbon atoms of the component (B) relative to the total mass of the measurement sample.

Gas Chromatograph Conditions:
Column: DB-1ht (manufactured by Agilent Technologies, Inc.)
Detector: flame ionization detector (FID)
Rate of temperature increase: 15° C./min
Column temperature: 50 to 350° C.
Standard substances: monoester having a total of 40 carbon atoms (for example, stearyl behenate), and monoester having a total of 48 carbon atoms (for example, tetracosanyl tetracosonate)

The stearyl behenate and tetracosanyl tetracosonate used as standard substances can be obtained, for example, by reacting behenic acid and stearyl alcohol, or lignoceric acid and lignoceryl alcohol in a molar ratio of 1:1, by heating the two compounds under a nitrogen atmosphere while removing the water that is produced. The monovalent fatty acids and monohydric alcohols used in preparing the standard substances may use compounds obtained commercially as chemical reagents (for example, from Tokyo Chemical Industry Co., Ltd.).

The monoester having a total of 40 to 48 carbon atoms of the component (B) contained in the solid wax composition according to the present invention may be only a single type of monoester, or may be a combination of two or more types. In the solid wax composition according to the present invention, the component (B) preferably contains one type, or two or more types, of monoesters of a linear saturated fatty acid of 18 to 22 carbon atoms and a linear saturated aliphatic alcohol of 18 to 22 carbon atoms, more preferably contains one type, or two or more types, of monoesters selected from the group consisting of stearyl behenate, nonadecanyl behenate, arachidyl behenate, henicosyl behenate, behenyl behenate and hydrogenated jojoba oil, even more preferably contains one type, or two or more types, of monoesters selected from the group consisting of behenyl behenate, stearyl behenate and hydrogenated jojoba oil, and most preferably contains behenyl behenate.

The mass ratio between the component (A) and the component (B) in the solid wax composition according to the present invention ([amount (mass) of the component (A)]: [amount (mass) of the component (B)]) is preferably within a range from 45:55 to 95:5, more preferably within a range from 60:40 to 80:20, and even more preferably within a range from 65:35 to 75:25. Ensuring that the content ratio between the component (A) and the component (B) falls within the above range means that when the solid wax composition is mixed with the oily component, satisfactory hardness and a satisfactory oil oozing suppression effect can be obtained, and a favorable texture and good storage stability can be achieved. In those cases where the solid wax composition according to the present invention contains two or more types of the component (B), the "amount of the component (B)" means the total amount of all the monoesters that correspond with the component (B). The mass ratio between the component (A) and the component (B) in the solid wax composition according to the present invention may be calculated from the mass ratio (blend ratio) between the component (A) and the component (B) that are added as raw materials.

The solid wax composition according to the present invention may also contain other components, provided that the effects achieved by including the component (A) and the component (B) in a specific content ratio are not impaired. Examples of these other components include monoesters and wax components other than the monoester of the component (B), impurities or contaminants derived from the synthesis or purification of the monoester of the component (B), and various additives that may be added for imparting or improving certain functions or properties. Examples of these additives include antioxidants, antioxidant aids, preservatives, and ultraviolet absorbers. These additives may be used individually, or a combination of two or more additives may be used.

Examples of the antioxidants include oil-soluble vitamin C derivatives, tocopherols and derivatives of tocopherols and salts thereof, dibutylhydroxytoluene, butylhydroxyanisole, and gallate esters. These antioxidants may be used individually, or a combination of two or more antioxidants may be used.

Examples of the antioxidant aids include phosphoric acid, citric acid, maleic acid, malonic acid, succinic acid, fumaric acid, cephalin, hexametaphosphate, phytic acid, and ethylenediaminetetraacetic acid.

Examples of the preservatives include methyl paraben, ethyl paraben, butyl paraben and phenoxyethanol. These preservatives may be used individually, or a combination of two or more preservatives may be used.

Examples of the ultraviolet absorbers include benzoic acid-based ultraviolet absorbers such as para-aminobenzoic acid (hereafter abbreviated as PABA), PABA monoglycerin ester, N,N-dipropoxy-PABA ethyl ester, N,N-diethoxy-PABA ethyl ester, N,N-dimethyl-PABA ethyl ester, N,N-dimethyl-PABA butyl ester and N,N-dimethyl-PABA ethyl ester; anthranilic acid-based ultraviolet absorbers such as homomethyl-N-acetyl anthranilate; salicylic acid-based ultraviolet absorbers such as amyl salicylate, menthyl salicylate, homomenthyl salicylate, octyl salicylate, phenyl salicylate, benzyl salicylate and p-isopropanol phenyl salicylate; cinnamic acid-based ultraviolet absorbers such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxycinnamate, isopropyl-p-methoxycinnamate, isoamyl-p-methoxycinnamate, octyl-p-methoxycinnamate (2-ethylhexyl-p-methoxycinnamate), 2-ethoxyethyl-p-methoxycinnamate, cyclohexyl-p-methoxycinnamate, ethyl-α-cyano-β-phenyl cinnamate, 2-ethylhexyl-α-cyano-β-phenyl cinnamate, and glyceryl mono-2-ethylhexanoyl-diparamethoxycinnamate; benzophenone-based ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenylbenzophenone-2-carboxylate, 2-hydroxy-4-n-octoxybenzophenone, and 4-hydroxy-3-carboxybenzophenone; as well as 3-(4'-methylbenzylidene)-d,l-camphor, 3-benzylidene-d,l-camphor, urocanic acid, urocanic acid ethyl ester, 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methylphenyl)benzotriazole, dibenzalazine, dianisoylmethane, 4-methoxy-4'-t-butyldibenzoylmethane, 5-(3,3-dimethyl-2-norbornylidene)-3-pentan-2-one, 2,4,6-trianilino-p-(carbo-T-ethylhexyl-1'-oxy)-1,3,5-triazine, 4-tert-butyl-4'-methoxydibenzoylmethane, hexyl ethylaminohydroxybenzoylbenzoate, ethylhexyltriazine, t-butylmethoxydibenzoylmethane, bis-ethylhexyloxyphenol methoxyphenyltriazine, diethylhexyl butamido triazone, and oxybenzone-3. These ultraviolet absorbers may be used individually, or a combination of two or more ultraviolet absorbers may be used.

In terms of the amounts of the component (A) and the component (B) in the solid wax composition according to the present invention, the ratio of the total amount (mass) of the two components relative to the total mass of the composition is preferably at least 70% by mass but not more than 100% by mass, more preferably at least 75% by mass but not more than 100% by mass, even more preferably at least 80% by mass but not more than 100% by mass, still more preferably at least 90% by mass but not more than 100% by mass, and particularly preferably at least 95% by mass but not more than 100% by mass. By ensuring that the ratio of the total amount (mass) of the component (A) and the component (B) relative to the total mass of the composition falls within the above range, the hardness improvement effect and oil oozing suppression effect provided by the component (A) and the component (B) can be satisfactorily realized when the solid wax composition is blended with the oily component.

The solid wax composition according to the present invention may be produced using any method that enables the component (A) and the component (B) to be mixed uniformly, and can be produced without the need for any special steps. For example, the solid wax composition according to the present invention can be produced by uniformly mixing the component (A) and the component (B) in a solid state in the desired blend ratio. Further, the solid wax composition according to the present invention can also be produced by heating and melting the component (A) and the component (B) in the desired blend ratio to generate a uniform mixture, and then cooling the mixture. The solid wax composition may also be molded into any desired shape such as flakes or granules during the cooling performed following the heating and melting.

When 15 g of the solid wax composition according to the present invention is heated and mixed with 85 g of di(caprylic acid/capric acid) propanediol to obtain a uniform mixture, and the resulting mixture is then poured into a circular cylindrical container (diameter: 38 mm, depth: 17 mm) and then cooled, the hardness of the obtained molded oil wax mixture is preferably at least 300 g, more preferably at least 300 g but not more than 800 g, even more preferably at least 400 g but not more than 800 g, and still more preferably at least 500 g but not more than 800 g. The hardness of this circular cylindrically molded oil wax mixture is measured using a gel hardness meter (product name: SD700, manufactured by Sun Scientific Co., Ltd.), and represents the stress (g) when a spherical plunger with a diameter of 5 mm is pushed 2.5 mm into the mixture.

When 15 g of the solid wax composition according to the present invention is heated and mixed with 85 g of di(caprylic acid/capric acid) propanediol to obtain a uniform mixture, the mixture is cooled, and 0.5 g of the resulting oil wax mixture is then placed on a filter paper for 0.5 hours, the surface area of the resulting oil ooze is preferably less than 10 cm$^2$, and more preferably less than 7 cm$^2$. The oil ooze surface area from 0.5 g of the oil wax mixture is measured by kneading the oil wax mixture with a paint knife until satisfactory fluidity is achieved, placing 0.5 g of the oil wax mixture in a circular shape with a diameter of 10 mm in the center of a filter paper (No. 2, manufactured by Advantec MFS, Inc., diameter: 90 mm) and then leaving the mixture to stand for 0.5 hours at room temperature of 25° C. (±2° C.), and represents the area of the filter paper that is discolored due to bleeding out of the oil component.

The solid wax composition according to the present invention can be used as a raw material for cosmetics, quasi-drugs, and medicines and the like. In particular, the solid wax composition according to the present invention has an excellent hardness adjustment action, and can be used favorably as a solidifying agent for various cosmetics, and is able to impart the cosmetics with excellent shape retention properties, an oil oozing suppression effect, a favorable texture, and good storage stability. Accordingly, the solid wax composition is ideal as a raw material for solid oily cosmetics, and particularly as a raw material for stick-type lipsticks and the like.

<Solid Oily Cosmetic>

A solid oily cosmetic according to the present invention contains a component (A): candelilla wax, and a component (B): a monoester having a total of 40 to 48 carbon atoms, wherein the mass ratio between the component (A) and the component (B) in the solid cosmetic ([amount (mass) of the component (A)]: [amount (mass) of the component (B)]) satisfies component (A):component (B)=45:55 to 95:5. The candelilla wax of the component (A) and the monoester of the component (B) contained in the solid oily cosmetic according to the present invention may use the same materials as the candelilla wax of the component (A) and the monoester of the component (B) respectively that represent the constituent components of the solid wax composition according to the present invention described above.

In the present invention and the present description, a "solid oily cosmetic" means a cosmetic which contains an oily component that is either liquid or paste-like at 20° C., and which is solid at normal temperature (20° C.).

The solid oily cosmetic according to the present invention preferably contains, as the component (B), one type, or two or more types, of monoesters of a linear saturated fatty acid of 18 to 22 carbon atoms and a linear saturated aliphatic alcohol of 18 to 22 carbon atoms, more preferably contains one or more monoesters selected from the group consisting of stearyl behenate, nonadecanyl behenate, arachidyl behenate, henicosyl behenate, behenyl behenate and hydrogenated jojoba oil, even more preferably contains one more monoesters selected from the group consisting of behenyl behenate, stearyl behenate and hydrogenated jojoba oil, and most preferably contains behenyl behenate. Further, the mass ratio between the component (A) and the component (B) in the solid oily cosmetic according to the present invention (component (A):component (B)) is preferably within a range from 45:55 to 95:5, more preferably within a range from 60:40 to 80:20, and even more preferably within a range from 65:35 to 75:25.

The component (B) that is included in the solid oily cosmetic according to the present invention may be a chemically synthesized compound, or may be a monoester contained in an oil fraction extracted from a natural product or a modified product thereof. Further, the raw material that is added for the purpose of incorporating the component (B) in the solid oily cosmetic according to the present invention need not necessarily be a material of high purity, and may be a crudely purified product of the reaction product of a chemical synthesis reaction, an oil fraction extracted from a natural product such as a plant or microorganism, or a modified product of such an oil fraction. This raw material has a ratio of the amount (mass) of the monoester having a total of 40 to 48 carbon atoms of the component (B) relative to the total mass of the raw material that is preferably at least 90% by mass but not more than 100% by mass, more preferably at least 94% by mass but not more than 100% by mass, and most preferably at least 96% by mass but not more than 100% by mass. This is because provided the amount satisfies this range, the hardness of the solid oily cosmetic can be further increased, and an improved oil oozing suppression effect is achieved.

The size of the effects of the present invention displayed by the solid oily cosmetic according to the present invention tends to be related to the total amount (mass) of the component (A) and the component (B) within the solid oily cosmetic. In particular, the size of the effects is directly affected by the total amount (mass) of the component (A) and the component (B) within the components excluding the powder components such as the extender pigments, colored pigments and pearl pigments described below. Accordingly, in those cases where the solid oily cosmetic according to the present invention contains powder components, it is appropriate that the preferred total amount (mass) of the component (A) and the component (B) in the solid oily cosmetic is calculated assuming that the components remaining following exclusion of the powder components from the raw materials of the solid oily cosmetic represent 100% by mass.

The lower limit for the proportion of the total amount (mass) of the component (A) and the component (B) in the solid oily cosmetic according to the present invention, assuming that the components excluding the powder components from the raw materials of the solid oily cosmetic represent 100% by mass, is preferably at least 5% by mass, more preferably at least 8% by mass, and even more preferably 10% by mass or greater. By ensuring that the lower limit for the total amount (mass) of the component (A) and the component (B) in the solid oily cosmetic according to the present invention is an amount that satisfies this range, and including the component (A) and the component (B) in the prescribed blend ratio, the hardness improvement effect and oil oozing suppression effect of the obtained solid oily cosmetic can be further enhanced.

Further, the upper limit for the proportion of the total amount (mass) of the component (A) and the component (B) in the solid oily cosmetic according to the present invention, assuming that the components excluding the powder components from the raw materials of the solid oily cosmetic represent 100% by mass, is preferably not more than 25% by mass, more preferably not more than 20% by mass, and even more preferably 18% by mass or less. By ensuring that the upper limit for the total amount (mass) of the component (A) and the component (B) in the solid oily cosmetic according to the present invention is an amount that satisfies this range, and including the component (A) and the component (B) in the prescribed blend ratio, the obtained solid oily cosmetic can be more easily adjusted to a hardness that yields a desirable texture.

The proportion of the total amount (mass) of the component (A) and the component (B) in the solid oily cosmetic according to the present invention, assuming that the total mass of the components excluding the powder components from the raw materials of the solid oily cosmetic represents 100% by mass, is preferably at least 5% by mass but not more than 25% by mass, more preferably at least 8% by mass but not more than 25% by mass, and even more preferably at least 10% by mass but not more than 25% by mass. Further, the total amount (mass) of the component (A) and the component (B) in the solid oily cosmetic according to the present invention, assuming that the components excluding the powder components from the raw materials of the solid oily cosmetic represent 100% by mass, is preferably at least 5% by mass but not more than 20% by mass, more preferably at least 5% by mass but not more than 18% by mass, even more preferably at least 8% by mass but not more than 18% by mass, and still more preferably at least 10% by mass but not more than 18% by mass.

In addition to the component (A) and the component (B), the solid oily cosmetic according to the present invention also contains an oil component described below. The oily component contained in the solid oily cosmetic according to the present invention may be liquid, paste-like or solid at 20° C. Further, the oily component contained in the solid oily cosmetic according to the present invention may be composed of a single component or two or more components. However, the oily component must contain at least one component that is liquid or paste-like at 20° C. For example, in those cases where the solid oily cosmetic contains two or more oily components, the solid oily cosmetic may contain both an oily component that is liquid or paste-like at 20° C., and an oily component that is solid at 20° C. The oily component contained in the solid oily cosmetic according to the present invention is preferably composed only of oily components that are liquid or paste-like at 20° C., and is more preferably composed only of oily components that are liquid at 20° C. (liquid oils).

The oily component is an oily component other than the component (A) and the component (B), and examples include hydrocarbons, fatty acid esters, triglycerides, fatty acids, higher alcohols, silicone oils, fluorine-based oils, and derivatives of these components. Specific examples include castor oil, olive oil, avocado oil, palm oil, cacao oil, liquid paraffin, liquid branched paraffin, Vaseline, squalane, hydrogenated polyisobutene, hydrogenated polydecene, di(caprylic acid/capric acid) propanediol, neopentyl glycol dicaprate, triethylhexanoin, butyl stearate, octyldodecyl myristate, isopropyl myristate, isopropyl lanolin fatty acid ester, hexyl lanolin fatty acid ester, diisopropyl adipate, diisopropyl sebacate, isotridecyl isononanoate, polyglyceryl decaisostearate, 2-octyldodecanol, diisostearyl malate, polyglyceryl-2 triisostearate, oleyl alcohol, dimethylpolysiloxane, methylphenylpolysiloxane, dimethylcyclopolysiloxane, methylhydrogenpolysiloxane, and perfluoropolyether.

The proportion of the amount (mass) of the oily component in the solid oily cosmetic according to the present invention, expressed relative to the total mass of the solid oily cosmetic, is preferably from 10 to 95% by mass, more preferably from 50 to 95% by mass, and even more preferably from 70 to 90% by mass.

The solid oily cosmetic according to the present invention may also contain other components besides the component (A), the component (B) and the oily component, provided that the effects achieved by including the component (A) and the component (B) in a specific content ratio are not impaired. Examples of these other components include powders and surfactants.

Extender pigments, colored pigments and pearl pigments may be used as the powders.

Examples of the extender pigments include inorganic pigments such as silicic acid, silicic anhydride, magnesium silicate, talc, sericite, mica, kaolin, clay, bentonite, bismuth oxychloride, zirconium oxide, magnesium oxide, zinc oxide, aluminum oxide, calcium sulfate, barium sulfate, magnesium sulfate, calcium carbonate and magnesium carbonate, and composite powders of these inorganic pigments; organic powders composed of a polyamide, polyester, polypropylene, polystyrene, polyurethane, nylon, silicone resin, vinyl resin, urea resin, phenol resin, silicon resin, acrylic resin, melamine resin, epoxy resin, polycarbonate resin, divinylbenzene-styrene copolymer, silk powder, cellulose, Nε-lauroyl-L-lysine, metal salt of a long-chain alkyl phosphoric acid, N-mono-long-chain alkylacyl basic amino acid or metal soap, and composite powders of these organic powders; and composite powders of an aforementioned inorganic powder and organic powder. The particle shape of these powders may be any shape, including spherical, plate-like, needle-like, granular and amorphous shapes.

Examples of the colored pigments include metal oxides such as titanium oxide, zinc oxide, yellow iron oxide, red iron oxide, black iron oxide, Prussian blue, ultramarine and chromium oxide, metal complexes such as manganese violet and cobalt titanate, as well as inorganic pigments such as carbon black, organic pigments such as tar-based colorants and lake pigments, and natural colorants such as carmine.

Examples of pearl pigments that may be used include pearl pigments prepared by coating mica or a synthetic phlogopite or the like with a colorant such as titanium oxide, iron oxide, silicon oxide, Prussian blue, chromium oxide, carmine, or an organic pigment or the like. These powders may be subjected to any of various surface treatments such as a water repellency treatment or a water and oil repellency treatment.

These powders may be used individually or in combinations of two or more powders, and are preferably included in the solid oily cosmetic according to the present invention in an amount of 5 to 50% by mass relative to the total mass of the entire solid oily cosmetic formulation.

For the surfactant, either one, or a combination of two or more nonionic surfactants, anionic surfactants, cationic surfactants, or amphoteric surfactants or the like may be used.

Examples of the nonionic surfactants include monoglycerides, sorbitan fatty acid esters, sucrose fatty acid esters, polyglycerol fatty acid esters, alkanolamides, amine oxides, polyoxyethylene alkyl ethers, polyethylene glycol fatty acid esters, polyoxyethylene sorbitan fatty acid esters, polyoxyethylene glycerol fatty acid esters, polyoxyethylene propylene glycol mono fatty acid esters, polyoxyethylene hydrogenated castor oil, polyoxyethylene fatty acid amides, polyoxyethylene alkyl amines, alkyl saccharides, α-monoalkyl glyceryl ethers, dimethylpolysiloxane-polyoxyalkylene copolymers, and dimethylpolysiloxane-monoalkyl glyceryl ether copolymers.

Examples of the anionic surfactant include alkylbenzene sulfonates, alkylnaphthalene sulfonates, polyoxyethylene alkyl ether sulfates, and polyoxyethylene lauryl ether phosphates.

Examples of the cationic surfactants include primary, secondary and tertiary amine salts and quaternary ammonium salts having an aliphatic hydrocarbon group.

Examples of the amphoteric surfactants include sodium β-laurylaminopropionate, lauryldimethylaminoacetic acid betaine, and 2-alkyl-N-carboxymethyl-N-hydroxyethylimidazolinium betaine.

In addition, lecithins and soybean saponin and the like may also be used as surfactants. Examples of the lecithins include lecithin, hydrogenated lecithin, lecithin hydroxide, lysolecithin, and hydrogenated lysolecithin. Further, examples of the hydrogenated lecithin include hydrogenated soybean phospholipid, hydrogenated rape phospholipid, and hydrogenated egg yolk phospholipid.

The solid oily cosmetic according to the present invention may also contain additives typically added to cosmetics, and water and the like, provided that the effects of the present invention are not impaired. Examples of these additives include antioxidants, antioxidant aids, preservatives, ultraviolet absorbers, monohydric alcohols, polyhydric alcohols, water-soluble polymers, pH adjusters, inorganic salts or salts of organic acids, chelating agents, vitamins, organic solvents, fragrances, various extracts, and ultraviolet scattering agents. These additives may be used individually, or a combination of two or more additives may be used.

The antioxidants, antioxidant aids, preservatives and ultraviolet absorbers may use the same compounds as those described above.

The monohydric alcohols may be lower alcohols or higher alcohols. Examples of the lower alcohols include methanol, ethanol, propanol, isopropanol, isobutyl alcohol, and t-butyl alcohol. Further, examples of the higher alcohols include cetanol (cetyl alcohol, palmityl alcohol), stearyl alcohol (octadecyl alcohol), isostearyl alcohol (isooctadecanol), oleyl alcohol, cetostearyl alcohol, octyldodecanol, decyltetradecanol, hexyldecanol, behenyl alcohol, lauryl alcohol, lanolin alcohol, and hydrogenated lanolin alcohol. A single monohydric alcohol may be used alone, or a combination of two or more monohydric alcohols may be used.

Examples of the polyhydric alcohols include propylene glycol (1,2-propanediol), 1,3-propanediol, 1,3-butylene glycol (1,3-butanediol), pentylene glycol (1,2-pentanediol), neopentyl glycol (2,2-dimethyl-1,3-propanediol), isoprene glycol (3-methyl-1,3-butanediol), dipropylene glycol, glycerol, diglycerol, polyglycerol, polyethylene glycol, pentaerythritol, dipentaerythritol, sorbitol, and sorbitan. A single polyhydric alcohol may be used alone, or a combination of two or more polyhydric alcohols may be used.

The water-soluble thickeners may be natural water-soluble polymers, semi-synthetic water-soluble polymers, or synthetic water-soluble polymers. The water-soluble thickener included in the solid oily cosmetic according to the present invention may be composed of a single material or a combination of two or more materials.

Examples of the natural water-soluble polymers include plant-based polymers such as agar, glucomannan, gum arabic, tragacanth gum, galactan, guar gum, carob gum, karaya gum, carrageenan, pectin, quince seeds (marmelo), algae colloid (brown algae extract) and starch (rice, corn, potato and wheat), microorganism-based polymers such as xanthan gum, dextran, succinoglucan and pullulan, and animal-based polymers such as collagen, casein, albumin and gelatin.

Examples of the semi-synthetic water-soluble polymers include starch-based polymers such as carboxymethyl starch and methylhydroxypropyl starch, cellulose-based polymers such as methyl cellulose, nitrocellulose, methylhydroxypropyl cellulose, sodium cellulose sulfate, hydroxypropyl cellulose, carboxymethyl cellulose, sodium carboxymethyl cellulose, crystalline cellulose and cellulose powder, and alginic acid-based polymers such as sodium alginate, and propylene glycol alginate.

Examples of the synthetic water-soluble polymers include vinyl-based polymers such as polyvinyl alcohol, polyvinyl methyl ether, polyvinylpyrrolidone and carboxy vinyl polymers, polyoxyethylene-based polymers such as polyethylene glycol 20,000, 40,000 and 60,000, as well as polyoxyethylene polyoxypropylene copolymer-based polymers, acrylic-based polymers such as sodium polyacrylate, poly (ethyl acrylate) and polyacrylamide, and polyethyleneimine and cationic polymers.

Examples of the pH adjusters include edetic acid, disodium edetate, citric acid, sodium citrate, sodium hydroxide, potassium hydroxide and triethanolamine. These pH adjusters may be used individually, or a combination of two or more pH adjusters may be used.

Examples of the inorganic salts include sodium chloride, potassium chloride, magnesium chloride, sodium sulfate, potassium sulfate and magnesium sulfate. Examples of the salts of organic acids include citric acid, malic acid and tartaric acid and salts thereof, ascorbic acid and salts thereof, and ascorbic acid derivatives and salts thereof.

Examples of the chelating agents include disodium edetate, edetic acid salts, and hydroxyethane diphosphonic acid and the like. These chelating agents may be used individually, or a combination of two or more chelating agents may be used.

Examples of the vitamins include vitamin A, vitamin B1, vitamin B2, vitamin B6, vitamin E, vitamin K, and derivatives of these vitamins, as well as pantothenic acid and derivatives thereof, and biotin.

Examples of the extracts include plant extracts from aloe vera, witch hazel, hamamelis, cucumber, lemon, lavender, and rose and the like.

The solid oily cosmetic according to the present invention can be produced using conventionally known cosmetic production methods. For example, the solid oily cosmetic can be produced by mixing all of the raw materials including the component (A), the component (B) and the oily component, and then molding the mixture into the desired shape. The raw material components may all be mixed at once, or may be mixed sequentially. The component (A) and the component (B) may be added as separate raw materials, or the solid wax composition according to the present invention may be used as a raw material. Further, during mixing, if necessary, mixing may be performed in a heated and melted state to facilitate uniform mixing.

There are no particular limitations on the shape of the solid oily cosmetic according to the present invention, and the shape may be selected appropriately in accordance with desired product quality. For example, the component (A), the component (B) and all of the other components may be heated and mixed to obtain a uniform mixture, and the resulting liquid or paste-like mixture may then be used to fill a container to produce the desired shape and then cooled. This yields a solid oily cosmetic of the desired shape. The solid oily cosmetic according to the present invention is preferably a stick-type cosmetic.

Examples of the types of solid oily cosmetics according to the present invention include lipstick, lip gloss, lip cream, lip liner, eye shadow, loose powder, eye blow, eye liner, rouge, solid powder, oily foundation, and concealer.

EXAMPLES

The present invention is described below in further detail based on a series of specific examples. However, the present invention is in no way limited to the content of the examples described below.

<Measurement of Amount of Monoester Having a Total of 40 to 48 Carbon Atoms>

In the following examples, the amount of the monoester having a total of 40 to 48 carbon atoms was determined by gas chromatography analysis under the analysis conditions described below, and was calculated as the ratio obtained by dividing the total peak area of those peaks appearing between the retention times corresponding with the main peaks of standard substances having a total of 40 and 48 carbon atoms by the total area of all the peaks.

Gas Chromatograph Conditions:

Column: DB-1ht (manufactured by Agilent Technologies, Inc.)

Detector: flame ionization detector (FID)

Rate of temperature increase: 15° C./min

Column temperature: 50 to 350° C.

Standard substances: monoester having a total of 40 carbon atoms (for example, stearyl behenate), and monoester having a total of 48 carbon atoms (for example, tetracosanyl tetracosonate)

[Synthesis Example 1] Behenyl Behenate

Under a nitrogen atmosphere, 340 g of behenic acid and 326 g of behenyl alcohol were reacted by heating at 250° C. for 15 hours while the water that was produced was removed, thus obtaining a monoester of Synthesis Example 1. The amount of monoester having a total of 40 to 48 carbon atoms within the obtained monoester was 99.6% by mass.

[Synthesis Example 2] Stearyl Behenate

Under a nitrogen atmosphere, 340 g of behenic acid and 270 g of stearyl alcohol were reacted by heating at 250° C. for 15 hours while the water that was produced was removed, thus obtaining a monoester of Synthesis Example 2. The amount of monoester having a total of 40 to 48 carbon atoms within the obtained monoester was 92.8% by mass.

[Synthesis Example 3] Stearyl Stearate

Under a nitrogen atmosphere, 284 g of stearic acid and 270 g of stearyl alcohol were reacted by heating at 250° C. for 15 hours while the water that was produced was removed, thus obtaining a monoester of Synthesis Example 3. The amount of monoester having a total of 40 to 48 carbon atoms within the obtained monoester was 0.0% by mass.

[Synthesis Example 4] Glyceryl Tribehenate

Under a nitrogen atmosphere, 340 g of behenic acid and 31.5 g of glycerol were reacted by heating at 250° C. for 15 hours while the water that was produced was removed, thus obtaining a monoester of Synthesis Example 4. The amount of monoester having a total of 40 to 48 carbon atoms within the obtained monoester was 0.0% by mass.

[Examples 1 to 15, Comparative Examples 1 to 10] Oil Wax Mixtures

Using the formulations shown in Tables 1 to 5, oil wax mixtures containing a liquid oil mixed with a solid wax composition were produced, and the hardness and oil oozing were then evaluated. The evaluation results are shown in Tables 1 to 5. The numerical values in the component cells in the tables represents "% by mass". Further, "A" and "B" in the tables correspond with the component (A) and the component (B) respectively of the solid wax composition according to the present invention. Further, in Tables 1 to 3, "(A):(B)" indicates the content ratio between the component (A) and the component (B) in each sample, whereas in Tables 4 and 5, "(A):(B)" indicates the content ratio between the component (A) or the component (A') and the component (B) or the component (B') in each sample.

<Raw Materials for Oil Wax Mixtures>

For the raw materials of the oil wax mixtures shown in Tables 1 to 5, the candelilla wax used "Purified Candelilla Wax SR-2" manufactured by Mitsuba Trading Co., Ltd., the carnauba wax used "Purified Carnauba Wax NC-1810" manufactured by Cerarica Noda Co., Ltd., the paraffin wax used "Paraffin 155" manufactured by Nippon Seiro Co., Ltd., the behenyl behenate used the material synthesized in Synthesis Example 1, the stearyl behenate used the material synthesized in Synthesis Example 2, the hydrogenated jojoba oil used "NIKKOL Jojoba Wax" manufactured by Nikko Chemicals Co., Ltd. (amount of monoester having 40 to 48 carbon atoms: 94.0% by mass), the stearyl stearate used the material synthesized in Synthesis Example 3, the glyceryl tribehenate used the material synthesized in Synthesis Example 4, the di(caprylic acid/capric acid) propanediol used "SALACOS PR-85" manufactured by The Nisshin OilliO Group, Ltd., the triethylhexanoin used "T.I.O" manufactured by The Nisshin OilliO Group, Ltd., the neopentyl glycol dicaprate used "ESTEMOL N-01" manufactured by The Nisshin OilliO Group, Ltd., and the hydrogenated polydecene used "NOMCORT HP-30" manufactured by The Nisshin OilliO Group, Ltd. In the tables, the numerical values within parentheses in the cells for behenyl behenate, stearyl behenate and hydrogenated jojoba oil indicate the amount of monoester having 40 to 48 carbon atoms (the blend amount multiplied by the fraction of monoester having 40 to 48 carbon atoms).

<Production of Oil Wax Mixtures>

Specifically, the component (A) and the component (A'), and the component (B) and the component (B') were heated to 100° C. and subjected to melting and mixing, and the mixture was then cooled to obtain a solid wax composition. Subsequently, the liquid oil was stirred and mixed with the obtained solid wax composition in a heated state at 100° C., and the resulting mixture was poured into a polycarbonate container (diameter: 38 mm, depth: 17 mm) and then cooled to room temperature, thus producing a circular cylindrical oil wax mixture.

<Hardness Evaluation>

Using a gel hardness meter (product name: SD700, manufactured by Sun Scientific Co., Ltd.), the stress (g) upon pushing a spherical plunger with a diameter of 5 mm 2.5 mm into the oil wax mixture in the polycarbonate container was measured and recorded as the hardness.

Hardness Evaluation Criteria:
  A: hardness of 600 g or greater
  B: hardness of at least 500 g but less than 600 g
  C: hardness of at least 300 g but less than 500 g
  D: hardness of at least 200 g but less than 300 g
  E: hardness of less than 200 g <Oil Oozing Evaluation>

About 5 g of the sample prepared for measuring the hardness was weighed onto a Petri dish, and was then kneaded with a paint knife until satisfactory fluidity was achieved, thus obtaining a sample for evaluating and measuring oil oozing. Subsequently, 0.5 g of this sample for evaluating and measuring oil oozing was placed in a circular shape with a diameter of 10 mm in the center of a filter paper (No. 2, manufactured by Advantec MFS, Inc., diameter: 90 mm), the sample was left to stand for 0.5 hours at room temperature of 25° C. (±2° C.), and a photograph was then taken. The area of the filter paper that had discolored due to bleeding out of the oil component was calculated by image processing. ImageJ was used as the image processing software.

Oil Oozing Evaluation Criteria:
  A: oil oozing of less than 6 $cm^2$
  B: oil oozing of at least 6 $cm^2$ but less than 7 $cm^2$
  C: oil oozing of at least 7 $cm^2$ but less than 10 $cm^2$
  D: oil oozing of at least 10 $cm^2$ but less than 15 $cm^2$
  E: oil oozing of 15 $cm^2$ or more

TABLE 1

| Constituent elements | | Raw materials | Examples | | | | |
| --- | --- | --- | --- | --- | --- | --- | --- |
| | | | 1 | 2 | 3 | 4 | 5 |
| Wax | (A) | Candelilla wax | 7.5 | 9 | 10.5 | 12 | 13.5 |
| | (A') | Carnauba wax | — | — | — | — | — |
| | | Paraffin wax | — | — | — | — | — |

TABLE 1-continued

|  |  |  | Examples | | | | |
| --- | --- | --- | --- | --- | --- | --- | --- |
| Constituent elements | | Raw materials | 1 | 2 | 3 | 4 | 5 |
| Monoester or Triester | (B) | Behenyl behenate | 7.5 (7.47) | 6 (5.98) | 4.5 (4.48) | 3 (2.99) | 1.5 (1.49) |
|  |  | Stearyl behenate | — | — | — | — | — |
|  |  | Hydrogenated jojoba oil | — | — | — | — | — |
|  | (B') | Stearyl stearate | — | — | — | — | — |
|  |  | Glyceryl tribehenate | — | — | — | — | — |
| Liquid oil |  | Di(caprylic acid/capric acid) propanediol | 85 | 85 | 85 | 85 | 85 |
|  |  | Triethylhexanoin | — | — | — | — | — |
|  |  | Neopentyl glycol dicaprate | — | — | — | — | — |
|  |  | Hydrogenated polydecene | — | — | — | — | — |
| (A):(B) |  |  | 50:50 | 60:40 | 70:30 | 80:20 | 90:10 |
| Effects |  | Hardness (evaluation) | C | B | A | C | C |
|  |  | Hardness (g) | 386 | 568.8 | 664.6 | 432 | 300.2 |
|  |  | Oil oozing (evaluation) | C | C | A | B | C |
|  |  | Oil oozing (cm$^2$) | 9.6 | 8.2 | 5.2 | 6.5 | 8.5 |

TABLE 2

|  |  |  | Examples | | | | | |
| --- | --- | --- | --- | --- | --- | --- | --- | --- |
| Constituent elements | | Raw materials | 6 | 7 | 8 | 9 | 10 | 11 |
| Wax | (A) | Candelilla wax | 6 | 7.5 | 12 | 10.5 | 10.5 | 10.5 |
|  | (A') | Carnauba wax | — | — | — | — | — | — |
|  |  | Paraffin wax | — | — | — | — | — | — |
| Monoester or Triester | (B) | Behenyl behenate | 4.5 (4.48) | 3.75 (3.74) | 1.5 (1.49) | 4.5 (4.48) | 4.5 (4.48) | 4.5 (4.48) |
|  |  | Stearyl behenate | — | — | — | — | — | — |
|  |  | Hydrogenated jojoba oil | — | — | — | — | — | — |
|  | (B') | Stearyl stearate | 4.5 | 3.75 | 1.5 | — | — | — |
|  |  | Glyceryl tribehenate | — | — | — | — | — | — |
| Liquid oil |  | Di(caprylic acid/capric acid) propanediol | 85 | 85 | 85 | — | — | — |
|  |  | Triethylhexanoin |  |  |  | 85 |  |  |
|  |  | Neopentyl glycol dicaprate |  |  |  |  | 85 |  |
|  |  | Hydrogenated polydecene |  |  |  |  |  | 85 |
| (A):(B) |  |  | 57:43 | 67:33 | 89:11 | 70:30 | 70:30 | 70:30 |
| Effects |  | Hardness (evaluation) | C | B | C | A | A | A |
|  |  | Hardness (g) | 479.6 | 581 | 364 | 766 | 668.6 | 692.2 |
|  |  | Oil oozing (evaluation) | — | — | — | A | A | A |
|  |  | Oil oozing (cm$^2$) | — | — | — | 4.0 | 5.2 | 5.2 |

TABLE 3

|  |  |  | Examples | | | |
| --- | --- | --- | --- | --- | --- | --- |
| Constituent elements | | Raw materials | 12 | 13 | 14 | 15 |
| Wax | (A) | Candelilla wax | 10.5 | 7.5 | 10.5 | 13.5 |
|  | (A') | Carnauba wax | — | — | — | — |
|  |  | Paraffin wax | — | — | — | — |
| Monoester or Triester | (B) | Behenyl behenate | — | — | — | — |
|  |  | Stearyl behenate | 4.5 (4.18) | — | — | — |
|  |  | Hydrogenated jojoba oil | — | 7.5 (7.05) | 4.5 (4.23) | 1.5 (1.41) |
|  | (B') | Stearyl stearate | — | — | — | — |
|  |  | Glyceryl tribehenate | — | — | — | — |
| Liquid oil |  | Di(caprylic acid/capric acid) propanediol | 85 | 85 | 85 | 85 |
|  |  | Triethylhexanoin | — | — | — | — |
|  |  | Neopentyl glycol dicaprate | — | — | — | — |
|  |  | Hydrogenated polydecene | — | — | — | — |
| (A):(B) |  |  | 72:28 | 52:48 | 71:29 | 91:9 |
| Effects |  | Hardness (evaluation) | C | C | B | C |
|  |  | Hardness (g) | 490.8 | 441.6 | 556.2 | 303.6 |
|  |  | Oil oozing (evaluation) | C | — | C | — |
|  |  | Oil oozing (cm$^2$) | 7.8 | — | 7.5 | — |

TABLE 4

| Constituent elements | | Raw materials | Comparative Examples | | | | |
|---|---|---|---|---|---|---|---|
| | | | 1 | 2 | 3 | 4 | 5 |
| Wax | (A) | Candelilla wax | — | — | 7.5 | 10.5 | 12 |
| | (A') | Carnauba wax | 10.5 | — | — | — | — |
| | | Paraffin wax | — | 10.5 | — | — | — |
| Monoester or Triester | (B) | Behenyl behenate | 4.5 (4.48) | 4.5 (4.48) | — | — | — |
| | | Stearyl behenate | — | — | — | — | — |
| | | Hydrogenated jojoba oil | — | — | — | — | — |
| | (B') | Stearyl stearate | — | — | 7.5 | 4.5 | 3 |
| | | Glyceryl tribehenate | — | — | — | — | — |
| Liquid oil | | Di(caprylic acid/capric acid) propanediol | 85 | 85 | 85 | 85 | 85 |
| | | Triethylhexanoin | — | — | — | — | — |
| | | Neopentyl glycol dicaprate | — | — | — | — | — |
| | | Hydrogenated polydecene | — | — | — | — | — |
| (A):(B) | | | 0:100 | 0:100 | 100:0 | 100:0 | 100:0 |
| [(A) + (A')]:[(B) + (B')] | | | 70:30 | 70:30 | 50:50 | 70:30 | 80:20 |
| Effects | | Hardness (evaluation) | E | C | E | D | D |
| | | Hardness (g) | 94.6 | 457.8 | 163.4 | 244.4 | 249.8 |
| | | Oil oozing (evaluation) | E | E | — | C | — |
| | | Oil oozing (cm$^2$) | 21.6 | 20.0 | — | 9.0 | — |

TABLE 5

| Constituent elements | | Raw materials | Comparative Examples | | | | |
|---|---|---|---|---|---|---|---|
| | | | 6 | 7 | 8 | 9 | 10 |
| Wax | (A) | Candelilla wax | 10.5 | — | 6 | 14.25 | 15 |
| | (A') | Carnauba wax | — | — | — | — | — |
| | | Paraffin wax | — | — | — | — | — |
| Monoester or Triester | (B) | Behenyl behenate | — | 15 (14.9) | 9 (8.96) | 0.75 (0.75) | — |
| | | Stearyl behenate | — | — | — | — | — |
| | | Hydrogenated jojoba oil | — | — | — | — | — |
| | (B') | Stearyl stearate | — | — | — | — | — |
| | | Glyceryl tribehenate | 4.5 | — | — | — | — |
| Liquid oil | | Di(caprylic acid/capric acid) propanediol | 85 | 85 | 85 | 85 | 85 |
| | | Triethylhexanoin | — | — | — | — | — |
| | | Neopentyl glycol dicaprate | — | — | — | — | — |
| | | Hydrogenated polydecene | — | — | — | — | — |
| (A):(B) | | | 100:0 | 0:100 | 40:60 | 95:5 | 100:0 |
| [(A) + (A')]:[(B) + (B')] | | | 70:30 | 0:100 | 40:60 | 95:5 | 100:0 |
| Effects | | Hardness (evaluation) | E | E | E | E | E |
| | | Hardness (g) | 72.5 | 196.2 | 175 | 187.2 | 120 |
| | | Oil oozing (evaluation) | C | E | D | C | C |
| | | Oil oozing (cm$^2$) | 9.8 | 23.8 | 14.6 | 9.5 | 9.4 |

These results revealed that the oil wax mixtures of Examples 1 to 11, which contained solid wax compositions containing the candelilla wax of the component (A) and the behenyl behenate of the component (B) in a ratio within a range from 45:55 to 95:5, were satisfactorily hard with a hardness of at least 300 g, and exhibited little oil oozing, regardless of the type of liquid oil used. In particular, based on the fact that even in the oil wax mixtures of Examples 6 to 8, which also included a monoester other than the component (B), favorable hardness and oil oozing resistance of similar levels to those of Examples 1 to 5 which contained only the monoester of the component (B) were able to be achieved, it was evident that the hardness improvement effect and oil oozing suppression effect obtained as a result of adding the component (A) and the component (B) in a ratio within a range from 45:55 to 95:5 was not significantly affected by other components, and should be achievable in cosmetics having all manner of formulations. Further, the results of Examples 12 to 15 confirmed that even when stearyl behenate or hydrogenated jojoba oil was used as the component (B), similar effects to those achieved using behenyl behenate were able to be obtained.

In contrast, in the case of the oil wax mixtures of Comparative Examples 1 and 2 which contained a wax other than the component (A), the level of oil oozing was severe, and particularly in the case of Comparative Example 1 which contained carnauba wax, the hardness was also very low. Furthermore, in the case of the oil wax mixtures of Comparative Examples 3 to 6 which contained an ester other than the component (B), the hardness was very low. Particularly in Comparative Examples 3 to 5, which contained stearyl stearate with the candelilla wax, based on the fact that absolutely no hardness improvement effect was observed, even when the blend amount of stearyl stearate was increased, it was evident that this hardness improvement effect was only obtainable by using a combination of candelilla wax and the specific monoester of the component (B).

Further, the oil wax mixtures of Comparative Examples 7 to 10 in which the blend ratio between the candelilla wax of the component (A) and the behenyl behenate of the component (B) was outside the range from 45:55 to 95:5 also exhibited unsatisfactory hardness. In particular, Comparative Example 8 in which the content ratio between the component (A) and the component (B) was 40:60 had a markedly lower hardness than the oil wax mixture of Example 1 in which the content ratio was 50:50, and Comparative Example 9 in which the content ratio was 95:5 had a markedly lower hardness than the oil wax mixture of Example 5 in which the content ratio was 90:10.

[Example 16, Comparative Examples 11 and 12]
Stick-Type Lip Creams

Stick-type lip creams were produced in accordance with the formulations shown in Table 6, and the storage stability and texture were evaluated. The results are shown in Table 6. The numerical values in the component cells in the table represents % by mass values.

<Raw Materials for Stick-Type Lip Creams>

For the raw materials of the stick-type lip creams shown in Table 6, the triethylhexanoin used "T.I.O" manufactured by The Nisshin OilliO Group, Ltd., the diisostearyl malate used "COSMOL 222" manufactured by The Nisshin OilliO Group, Ltd., the polyglyceryl-2 diisostearate used "COSMOL 42V" manufactured by The Nisshin OilliO Group, the polyglyceryl-2 triisostearate used "COSMOL 43V" manufactured by The Nisshin OilliO Group, the hydrogenated polyisobutene used "PARLEAM 18" manufactured by NOF Corporation, the candelilla wax used "Purified Candelilla Wax SR-2" manufactured by Mitsuba Trading Co., Ltd., the behenyl behenate used the material synthesized in Synthesis Example 1, the microcrystalline wax used "MULTIWAX W445" manufactured by Sonneborn LLC, and the paraffin wax used "Paraffin 155" manufactured by Nippon Seiro Co., Ltd.

The component (A) and the component (B) shown in Table 6 were heated to 100° C., and following melting and mixing, the mixture was cooled to obtain a solid wax composition. The other components were added to the obtained solid wax composition, and following stirring and mixing in a heated state at 100° C., the resulting mixture was poured into a bullet-shaped lipstick mold and then cooled to room temperature, thus obtaining a stick-type lip cream. For evaluation of the texture, the amount of the wax was adjusted so that the similar hardness might be achieved, and the blend amount of one of the liquid oils was adjusted to make the total amount of components up to 100% by mass.

<Evaluation of Storage Stability>

For each lip cream, the storage stability was evaluated using the change in hardness as an indicator. Specifically, the hardness (a) of the lip cream immediately following production, and the hardness (b) of the lip cream following a cycled storage test in which the steps of storing the lip cream at 5° C. for 12 hours and then storing the lip cream at 40° C. for 12 hours were repeated for two weeks were measured, and the degree of change [(b)/(a)] was determined. A higher value for this degree of change was evaluated as indicating superior storage stability.

<Evaluation of Texture>

Each lip cream was evaluated by five specialist panelists for "resistance to oil oozing", "adhesion", "spreadability" and "degree of gloss", by comparing the lip cream with a commercially available lip cream, and assigning an evaluation of "superior", "similar" or "inferior" for each category. The results are shown in Table 6.

Evaluation Criteria for Texture:
A: at least three of the five panelists evaluated the lip cream as "superior" to the commercially available lip cream
B: neither A nor C
C: at least three of the five panelists evaluated the lip cream as "inferior" to the commercially available lip cream

TABLE 6

| | Raw materials | Comparative Example 11 | Comparative Example 12 | Example 16 |
|---|---|---|---|---|
| Liquid oil | Triethylhexanoin | 16 | 16 | 16 |
| | Diisostearyl malate | 20 | 20 | 20 |
| | Squalane | 10 | 10 | 10 |
| | Polyglyceryl-2 diisostearate | 17 | 17 | 17 |
| | Polyglyceryl-2 triisostearate | 17 | 18 | 20 |
| | Hydrogenated polyisobutene | 5 | 5 | 5 |
| (A) | Candelilla wax | — | 14 | 8.4 |
| (B) | Behenyl behenate (Synthesis Example 1) | — | — | 3.6 (3.59) |
| Other components | Microcrystalline wax | 3 | — | — |
| | Paraffin wax | 12 | — | — |
| Total amount of wax (% by mass) | | 15 | 14 | 13 |
| (A):(B) | | — | 100:0 | 70:30 |
| Hardness (g) (a) | | 414.2 | 424.3 | 425.4 |
| Hardness (g) (after 2 weeks cycling between 5° C. and 40° C.) (b) | | 276.9 | 302.9 | 362.9 |
| Degree of change (b)/(a) | | 0.67 | 0.71 | 0.85 |
| Evaluations | Adhesion | B | B | A |
| | Spreadability | B | A | A |
| | Resistance to oil oozing | B | C | B |
| | Degree of gloss | B | A | A |

The lip cream of Example 16 had satisfactory hardness as a stick-type cosmetic, suffered little oil oozing during use, had a favorable texture, and also exhibited good storage stability. Lip creams tend to suffer a decreases in hardness when subjected to repeated temperature changes, which can sometimes cause the lip stick to break during use, but it was confirmed that the solid oily cosmetic containing the solid wax composition according to the present invention was resistant to deterioration in the hardness during storage, meaning this concern can be minimized.

[Formulation Example 1] Lipstick (Stick-Type)

<Raw Materials for Lipstick (Stick-Type)>

For the raw materials of the lipstick shown in Table 7, the pentaerythrityl tetraisostearate used "SALACOS 5418V" manufactured by The Nisshin OilliO Group, Ltd., the glyceryl tri(caprylate/tricaprate) used "O.D.O." manufactured by The Nisshin OilliO Group, Ltd., the hydrogenated polyisobutene used "PARLEAM 18" manufactured by NOF Corporation, the diisostearyl malate used "COSMOL 222" manufactured by The Nisshin OilliO Group, the polyglyceryl-2 triisostearate used "COSMOL 43V" manufactured by The Nisshin OilliO Group, the dipentaerythrityl hexa(hydroxystearate/stearate/rosinate) used "COSMOL 168ARV" manufactured by The Nisshin OilliO Group, the glyceryl (ethylhexanoate/stearate/adipate) used "NOMCORT LAH" manufactured by The Nisshin OilliO Group, the candelilla wax used "Purified Candelilla Wax SR-2" manufactured by Mitsuba Trading Co., Ltd., and the behenyl behenate used the material synthesized in Synthesis Example 1.

Of the raw materials shown in Table 7, the candelilla wax and the behenyl behenate were heated to 100° C., and following melting and mixing, the mixture was cooled to obtain a solid wax composition. The other components were added to this solid wax composition, and following thorough mixing under heating at 90° C. to obtain a uniform mixture, the mixture was degassed under reduced pressure, and then poured into a mold. Subsequently, the mixture was cooled to 20° C. to obtain a lipstick (stick-type). In this case, the proportion representing the total mass of the candelilla wax and the behenyl behenate relative to the total mass of the lipstick excluding the powder components (red color No. 201, red color No. 202, and titanated mica) was about 17% by mass.

TABLE 7

| Raw materials | Amount (% by mass) |
| --- | --- |
| Pentaerythrityl tetraisostearate | 16 |
| Glyceryl tri(caprylate/caprate) | 16 |
| Squalane | 10 |
| Hydrogenated polyisobutene | 4 |
| Diisostearyl malate | 10 |
| Polyglyceryl-2 triisostearate | 10 |
| Dipentaerythrityl hexa(hydroxystearate/stearate/rosinate) | 4 |
| Glyceryl (ethylhexanoate/stearate/adipate) | 2 |
| Di(phytosteryl/octyldodecyl) lauroylglutamate | 5 |
| Candelilla wax | 11.2 |
| Behenyl behenate (Synthesis Example 1) | 4.8 (4.78) |
| Red color No. 201 | 1 |
| Red color No. 202 | 2 |
| Titanated mica | 4 |
| Total | 100 |

[Formulation Example 2] Lipstick (Stick-Type)

Using the formulation shown in Table 8, the same procedure as Formulation Example 1 was used to produce a lipstick (stick-type). In this case, the proportion representing the total mass of the candelilla wax, the behenyl behenate and the hydrogenated jojoba oil relative to the total mass of the lipstick excluding the powder components (red color No. 201, red color No. 202, and titanated mica) was about 17% by mass.

<Raw Materials for Lipstick (Stick-Type)>

For the raw materials of the lipstick shown in Table 8, the neopentyl glycol dicaprate used "ESTEMOL N-01" manufactured by The Nisshin OilliO Group, Ltd., the phenyl trimethicone used "SH556 Fluid" manufactured by Dow Corning Toray Co., Ltd., the dipentaerythrityl pentaisostearate used "SALACOS DP-518N" manufactured by The Nisshin OilliO Group, Ltd., the hydrogenated polyisobutene used "PARLEAM 24" manufactured by NOF Corporation, the diisostearyl malate used "COSMOL 222" manufactured by The Nisshin OilliO Group, the dipentaerythrityl hexahydroxystearate used "COSMOL 168M" manufactured by The Nisshin OilliO Group, the dipentaerythrityl tetra(hydroxystearate/isostearate) used "COSMOL 168EV" manufactured by The Nisshin OilliO Group, the dipentaerythrityl tripolyhydroxystearate used "SALACOS WO-6" manufactured by The Nisshin OilliO Group, the candelilla wax used "Purified Candelilla Wax SR-2" manufactured by Mitsuba Trading Co., Ltd., and the behenyl behenate used the material synthesized in Synthesis Example 1.

TABLE 8

| Raw materials | Amount (% by mass) |
| --- | --- |
| Polyglyceryl-10 decaisostearate | 15 |
| Neopentyl glycol dicaprate | 27.5 |
| Phenyl trimethicone | 10 |
| Dipentaerythrityl pentaisostearate | 4 |
| Hydrogenated polyisobutene | 2 |
| Diisostearyl malate | 8 |
| Octyldodecanol | 5 |
| Dipentaerythrityl hexahydroxystearate | 4 |
| Dipentaerythrityl tetra(hydroxystearate/isostearate) | 2 |
| Dipentaerythrityl tripolyhydroxystearate | 1 |
| Dimer dilinoleyl bis(behenyl/isostearyl/phytosteryl) dimer dilinoleate | 1 |
| Candelilla wax | 11.2 |
| Behenyl behenate (Synthesis Example 1) | 2.4 (2.39) |
| Hydrogenated jojoba oil | 2.4 |
| Red color No. 201 | 0.5 |
| Red color No. 202 | 2 |
| Titanated mica | 2 |
| Total | 100 |

[Formulation Example 3] Oily Foundation

Using the formulation shown in Table 9, with the exception of replacing the mold with a metal dish, the same procedure as Formulation Example 1 was used to produce an oily foundation. In this case, the proportion representing the total mass of the candelilla wax and the behenyl behenate relative to the total mass of the oily foundation excluding the powder components (titanium oxide, kaolin talc, nylon powder, iron oxide (black), iron oxide (yellow), and red iron oxide) was about 17% by mass.

<Raw Materials for Oily Foundation>

For the raw materials of the oily foundation shown in Table 9, the cetyl ethylhexanoate used "SALACOS 816T" manufactured by The Nisshin OilliO Group, Ltd., the polyglyceryl-2 triisostearate used "COSMOL 43V" manufactured by The Nisshin OilliO Group, the candelilla wax used "Purified Candelilla Wax SR-2" manufactured by Mitsuba Trading Co., Ltd., and the behenyl behenate used the material synthesized in Synthesis Example 1.

TABLE 9

| Raw materials | Amount (% by mass) |
| --- | --- |
| Mineral oil | 15 |
| Cetyl ethylhexanoate | 28.45 |
| Polyglyceryl-2 triisostearate | 5 |
| Microcrystalline wax | 0.5 |
| Candelilla wax | 7 |
| Behenyl behenate | 3 |
| (Synthesis Example 1) | (2.99) |
| Titanium oxide | 15 |
| Kaolin | 10 |
| Talc | 8 |
| Nylon powder | 3 |
| Iron oxide (black) | 0.05 |
| Iron oxide (yellow) | 4 |
| Red iron oxide | 1 |
| Total | 100 |

The invention claimed is:

1. A solid wax composition comprising
a component (A): candelilla wax, and
a component (B): a monoester having a total of 40 to 48 carbon atoms, wherein
a mass ratio between the component (A) and the component (B) in the solid wax composition satisfies component (A):component (B)=57:43 to 80:20, and
the monoester is a monoester of a monovalent linear saturated fatty acid of 18 to 22 carbon atoms and a monohydric linear saturated aliphatic alcohol of 18 to 22 carbon atoms.

2. The solid wax composition according to claim 1, wherein the monoester of the component (B) comprises behenyl behenate.

3. The solid wax composition according to claim 1, wherein a proportion representing a sum of amounts of the component (A) and the component (B) relative to a total mass of the composition is at least 90% by mass.

4. The solid wax composition according to claim 1, wherein a proportion representing a sum of amounts of the component (A) and the component (B) relative to a total mass of the composition is at least 96% by mass.

5. The solid wax composition according to claim 1, wherein the monoester is selected from the group consisting of behenyl stearate, arachidyl eicosanoate, henicosyl eicosanoate, behenyl eicosanoate, stearyl behenate, nonadecanyl behenate, arachidyl behenate, henicosyl behenate, and behenyl behenate.

6. The solid wax composition according to claim 1, wherein the monoester is selected from the group consisting of stearyl behenate and behenyl behenate.

7. The solid wax composition according to claim 1, wherein the monoester comprises behenyl behenate.

8. The solid wax composition according to claim 1, wherein the monoester is selected from the group consisting of stearyl behenate, nonadecanyl behenate, arachidyl behenate, henicosyl behenate, and behenyl behenate.

9. The solid wax composition according to claim 1, wherein the solid wax composition is free of monoesters other than the component (B).

10. A solid oily cosmetic comprising the solid wax composition of claim 1.

11. The solid oily cosmetic according to claim 10, wherein a proportion representing a sum of amounts of the component (A) and the component (B) relative to a total mass of the solid wax composition is at least 90% by mass.

12. The solid oily cosmetic according to claim 10, further comprising a liquid oil.

13. The solid oily cosmetic according to claim 10, further comprising at least one surfactant selected from the group consisting of nonionic surfactants, anionic surfactants, cationic surfactants, or amphoteric surfactants.

14. The solid oily cosmetic according to claim 10, further comprising powders selected from the group consisting of extender pigments, colored pigments and pearl pigments.

15. A solid oily cosmetic comprising
a component (A): candelilla wax, and
a component (B): a monoester having a total of 40 to 48 carbon atoms, wherein
a mass ratio between the component (A) and the component (B) in the solid oily cosmetic satisfies component (A):component (B)=57:43 to 80:20, and
the monoester is a monoester of a monovalent linear saturated fatty acid of 18 to 22 carbon atoms and a monohydric linear saturated aliphatic alcohol of 18 to 22 carbon atoms.

16. The solid oily cosmetic according to claim 15, further comprising an oil component.

17. The solid oily cosmetic according to claim 16, wherein the oil component comprises a liquid oil.

18. The solid oily cosmetic according to claim 16, wherein the oil component comprises at least one component selected from the group consisting of hydrocarbons, fatty acid esters, triglycerides, fatty acids, higher alcohols, silicone oils, and fluorine-based oils.

19. The solid oily cosmetic according to claim 15, further comprising an oil component in an amount from 10 to 95% by mass based on total mass of the solid oily cosmetic.

20. The solid oily cosmetic according to claim 15, further comprising an oil component, and
powders selected from the group consisting of extender pigments, colored pigments and pearl pigments.

21. The solid oily cosmetic according to claim 15, further comprising an oil component, and
at least one surfactant selected from the group consisting of nonionic surfactants, anionic surfactants, cationic surfactants, or amphoteric surfactants.

22. The solid oily cosmetic according to claim 16, wherein the oil component comprises at least one component selected from the group consisting of castor oil, olive oil, avocado oil, palm oil, cacao oil, liquid paraffin, liquid branched paraffin, Vaseline, squalane, hydrogenated polyisobutene, hydrogenated polydecene, di(caprylic acid/capric acid) propanediol, neopentyl glycol dicaprate, triethylhexanoin, butyl stearate, octyldodecyl myristate, isopropyl myristate, isopropyl lanolin fatty acid ester, hexyl lanolin fatty acid ester, diisopropyl adipate, diisopropyl sebacate, isotridecyl isononanoate, polyglyceryl decaisostearate, 2-octyldodecanol, diisostearyl malate, polyglyceryl-2 triisostearate, oleyl alcohol, dimethylpolysiloxane, methylphenylpolysiloxane, dimethylcyclopolysiloxane, methylhydrogenpolysiloxane, and perfluoropolyether.

23. A solid wax composition comprising
a component (A): candelilla wax, and
a component (B): a monoester having a total of 40 to 48 carbon atoms, wherein
a mass ratio between the component (A) and the component (B) in the solid wax composition satisfies component (A):component (B)=45:55 to 95:5, the monoester is a monoester of a monovalent fatty acid and a monohydric alcohol, and a proportion representing a sum of amounts of the component (A) and the component (B) relative to a total of the composition is at least 90% by mass.

24. The solid wax composition according to claim 23, wherein the mass ratio between the component (A) and the component (B) in the solid wax composition satisfies component (A):component (B)=57:43 to 80:20.

25. The solid wax composition according to claim 23, wherein the monoester comprises a monoester of a monovalent linear saturated fatty acid of 18 to 22 carbon atoms and a monohydric linear saturated aliphatic alcohol of 18 to 22 carbon atoms.

26. The solid wax composition according to claim 23, wherein the monoester is selected from the group consisting of behenyl stearate, arachidyl eicosanoate, henicosyl eicosanoate, behenyl eicosanoate, stearyl behenate, nonadecanyl behenate, arachidyl behenate, henicosyl behenate, and behenyl behenate.

27. A solid oily cosmetic comprising the solid wax composition of claim 23.

28. The solid oily cosmetic according to claim 27, wherein a proportion representing a sum of amounts of the component (A) and the component (B) relative to a total mass of the solid wax composition is at least 90% by mass.

29. The solid oily cosmetic according to claim 27, further comprising a liquid oil.

30. The solid oily cosmetic according to claim 27, further comprising at least one surfactant selected from the group consisting of nonionic surfactants, anionic surfactants, cationic surfactants, or amphoteric surfactants.

31. The solid oily cosmetic according to claim 27, further comprising powders selected from the group consisting of extender pigments, colored pigments and pearl pigments.

* * * * *